United States Patent [19]

Sanderson et al.

[11] Patent Number: 5,025,113

[45] Date of Patent: Jun. 18, 1991

[54] CATALYTIC PREPARATION OF TERTIARY BUTYL ALCOHOL FROM TERTIARY BUTYL HYDROPEROXIDE

[75] Inventors: John R. Sanderson, Leander; John F. Knifton, Austin, both of Tex.

[73] Assignee: Texaco Chemical Company, White Plains, N.Y.

[21] Appl. No.: 471,450

[22] Filed: Jan. 29, 1990

[51] Int. Cl.[5] ..................... C07C 29/132; C07C 31/12
[52] U.S. Cl. .................. 568/909.8; 568/715; 568/840; 568/864
[58] Field of Search ............. 568/715, 815, 840, 864, 568/573, 571, 909.8

[56] References Cited

U.S. PATENT DOCUMENTS 4,551,553 11/1985 Taylor et al. ............... 568/815
4,922,033 5/1990 Sanderson et al. .......... 568/909.8
4,922,034 5/1990 Sanderson et al. .......... 568/909.8

Primary Examiner—Werren B. Lone
Attorney, Agent, or Firm—Jack H. Park; Kenneth R. Priem; Carl C. Ries

[57] ABSTRACT

A tertiary butyl hydroperoxide feedstock, such as one prepared from the reaction product formed by the reaction of isobutane with molecular oxygen and which feedstock comprises tertiary butyl hydroperoxide dissolved in tertiary butyl alcohol, is charged to a catalytic decomposition zone where the tertiary butyl hydroperoxide is catalytically decomposed in the presence of a soluble catalyst system to provide a decomposition reaction product characterized by a high conversion rate and a high selectivity of tertiary butyl hydroperoxide to tertiary butyl alcohol, the catalyst system being composed of a soluble iron compound and a soluble ruthenium compound.

6 Claims, No Drawings

CATALYTIC PREPARATION OF TERTIARY BUTYL ALCOHOL FROM TERTIARY BUTYL HYDROPEROXIDE

BACKGROUND OF THE INVENTION

1. Field of the Invention

This invention relates to the catalytic decomposition of tertiary butyl hydroperoxide. More particularly, this invention relates to a method for the preparation of tertiary butyl alcohol by the catalytic decomposition of tertiary butyl hydroperoxide. Still more particularly, this invention relates to a method wherein a soluble catalyst system composed of a soluble iron compound and a soluble ruthenium compound is used to catalyze the substantially selective decomposition of tertiary butyl hydroperoxide to tertiary butyl alcohol.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroperoxide to form tertiary butyl alcohol.

In the text entitled "Organic Peroxides" edited by Daniel Swern (Wiley Interscience, a Division of John Wiley & Sons, New York), in Vol. II on page 157 it is stated that the metal-ion-catalyzed decomposition of primary hydroperoxides yields mainly alcohols, aldehydes and carboxylic acids, citing as an example the decomposition of hydroxymethyl hydroperoxide with aqueous ferrous sulfate to provide formaldehyde, formic acid and water.

Quin U S. Pat. No. 2,854,487 discloses the hydrogenation of hydrocarbon peroxides in the presence of hydrogen and palladium on activated alumina to provide carbinols.

In Massie U.S. Pat. No. 3,775,472 a process is disclosed wherein alkyl substituted aromatic hydrocarbons are oxidized to products such as aromatic alcohols, aldehydes and carboxylic acids in the presence of ruthenium compounds.

Vanadium and ruthenium catalysts have been used to prepare saturated vicinal esters by catalyzing the reaction of olefins and the carboxylic acid derivatives thereof with oxygen, as shown by Stapp U.S. Pat. No. 4,221,916.

Taylor et al. U.S. Pat. No. 4,551,553 is directed to a process for the formation of alcohols such as tertiary butyl alcohol by the catalytic decomposition of an organic hydroperoxide such as tertiary butyl hydroperoxide using a binary catalyst composed of a mixture of a ruthenium compound with a chromium compound. It is stated that the use of the binary catalyst eliminates the need for stabilizing ligands.

Quin U.S. Pat. No. 2,854,487 discloses a process wherein isopropyl benzene hydroperoxides are catalytically decomposed to form carbonols in the presence of hydrogen and a catalyst composed of palladium supported on activated alumina.

Grane U.S. Pat. No. 3,474,151 discloses that tertiary butyl alcohol starts to dehydrate at 450° C. and to decompose at a "rapid rate" at temperatures above 475° F. Grane discovered, however, that residual quantities of hydroperoxide contaminants present in tertiary butyl alcohol could be thermally decomposed by heating the contaminated tertiary butyl alcohol at a temperature of 375° to 475° F. for about 1 to 10 minutes.

Grane et al. U.S. Pat. No. 4,294,999 discloses a process wherein isobutane is oxidized in a pressured reactor in the presence of a solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,151 by heating the tertiary butyl alcohol at 375° to 475° for about 1 to 10 minutes. Heating tertiary butyl alcohol containing small amounts of peroxides at high temperatures for even short periods of time to remove the peroxides produces undesirable products such as isobutylene.

Grane et al. U.S. Pat. No. 4,296,262 discloses a related process wherein isobutane is reacted with oxygen in a reaction zone for a residence time of about 1 to 10 hours at a temperature of about 240° to about 340° F. and a pressure of about 100 to about 1000 psig. in the presence of a catalytically effective amount of a soluble molybdenum catalyst. A liquid stream comprising tertiary butyl alcohol is recovered from the reaction mixture and fed to a decomposition zone wherein the tertiary butyl hydroperoxide contained therein is decomposed by "hot aging" at 250°–350° F. at a pressure lower than the pressure in the oxidation zone. The tertiary butyl alcohol can be further subjected to a cleanup treatment at 375°–475° F. for 1 to 10 minutes. Worrell et al. in U.S. Pat. No. 4,296,263 disclose a related process wherein the feedstock is a mixture of normal butane with isobutane and wherein the oxidation catalyst is a soluble form of chromium, cobalt, nickel, manganese, molybdenum, or a mixture thereof.

BACKGROUND INFORMATION

The catalytic decomposition of tertiary butyl hydroperoxide to preferentially form tertiary butyl alcohol is disclosed ion a number of U.S. patents that were copending with this application, such as Sanderson et al. U.S. Pat. No. 4,922,033 based on an application filed Sept. 8, 1987 and entitled: "Preparation of Tertiary Butyl Alcohol by the Catalytic Decomposition of Tertiary Butyl Hydroperoxide" Sanderson et al. filed Sept. 8, 1987 and entitled: "Catalytic Decomposition of Tertiary Butyl Hydroperoxide" U.S. Pat. No. 4,922,034, based on an application filed Sep. 8, 1987 and entitled: ∓Catalytic Conversion of Tertiary Butyl Hydroperoxide to Tertiary Butyl Alcohol" Sanderson et al. U.S. Pat. No. 4,912,266, based on an application Sanderson et al. U.S. Pat. No. 4,910,349 based on an application Tertiary Butyl Alcohol by the Catalytic Decomposition of Sanderson et al. U.S. Pat. No. 4,912,267 based on an application and entitled: "Catalytic Conversion of Tertiary Butyl Hydroperoxide to Tertiary Butyl Alcohol" Sanderson et al., U.S. Pat. No. 4,922,036 based on an application Tertiary Butyl Hydroperoxide Decomposition" Sanderson et al. U.S. Pat. No. 4,922,035 based on an application and entitled: "Catalytic Preparation of Tertiary Butyl Alcohol by Decomposition of Tertiary Butyl Hydroperoxide". Sanderson et al. U.S. Pat. No. 4,912,267 based on an application filed Sept. 8 1967, and entitled "Catalytic Conversion of Tertiary Butyl Hydroperoxide to Tertiary Butyl Alcohol" Sanderson et al. U.S. Pat. No. 4,922,036 based on an application filed Sep. 8, 1987 and entitled: "Tertiary Butyl Hydroperoxide Decomposition" and Sanderson et al. U.S. Pat. No. 4,922,035 based on an application filed Sep. 8, 1987 and entitled: "Catalytic Preparation of Tertiary Butyl Alcohol by Decomposition of Tertiary Butyl Hydroperoxide".

When isobutane is reacted with molecular oxygen, the principal products of the reaction are tertiary butyl alcohol and tertiary butyl hydroperoxide. However, minor amounts of other contaminants are also formed.

In addition, a minor amount of water will be formed, which will normally amount to about 0.5 to 1 wt. % of the reactor effluent. The amount of byproduct water that is produced is a function of the severity of the reaction conditions employed and will tend to increase as the severity of the reaction conditions is increased.

A listing of the components present in a representative reaction product, and their nominal boiling points is given in Table A.

TABLE A

| Component | NBP (°C.) |
|---|---|
| Isobutane | −11.7 |
| Methyl formate | 31.8 |
| Acetone | 56.3 |
| Isobutylene oxide | 60.0 |
| Isobutyraldehyde | 64.1 |
| Methanol | 64.7 |
| Methyl-t-butyl peroxide | 74.2 |
| Isopropyl alcohol | 82.3 |
| Tertiary butyl alcohol | 82.4 |
| Ditertiary butyl peroxide | 111.0 |
| t-butyl-i-pr-peroxide | 124.0 |
| Tertiary butyl formate | 163.8 |

The minor by-products are sometimes difficult to remove. For example, tertiary butyl formate has a higher boiling point than ditertiary butyl hydroperoxide but tends to distill overhead, which suggests that it forms a minimum boiling azeotrope with another component or components.

As indicated, tertiary butyl hydroperoxide is useful as a raw material for the manufacture of tertiary butyl alcohol. The tertiary butyl alcohol can be formed by catalytic decomposition of the tertiary butyl hydroperoxide. In the Williams et al. process disclosed in U.S. Pat. No. 3,472,876, an oxygen-containing gas was charged to a reactor containing isobutane and an oxidation catalyst to provide a reaction mixture comprising tertiary butyl alcohol, tertiary butyl hydroperoxide, acetone, and tertiary butyl ether. The reported results in the patent indicate that there was a comparatively low rate of conversion and a comparatively poor selectivity of the reaction to tertiary butyl alcohol.

SUMMARY OF THE INVENTION

A feedstock for the present invention is suitably one by the oxidation of isobutane with molecular oxygen to provide an oxidation reaction product containing a solution of tertiary butyl hydroperoxide and tertiary butyl alcohol in unreacted isobutane. The feedstock for the present invention may comprise tertiary butyl hydroperoxide dissolved in tertiary butyl alcohol which is recovered from the isobutane oxidation reaction product. The feedstock is charged to a catalytic decomposition zone wherein the tertiary butyl hydroperoxide is decomposed in the presence of a soluble catalyst system composed of a soluble iron compound and a soluble ruthenium compound to provide a decomposition reaction product characterized by a high conversion rate and a high selectivity of tertiary butyl hydroperoxide to tertiary butyl alcohol.

The tertiary butyl alcohol will not be the only decomposition product that is formed. Minor amounts of other oxygen-containing materials such as those listed above will also be formed.

The tertiary butyl alcohol that is recovered from the decomposition reaction mixture will be contaminated with the oxygenated impurities.

DESCRIPTION OF THE PROCESS OF THE PRESENT INVENTION

The starting materials for the process of the present invention are a tertiary butyl hydroperoxide feedstock and a catalyst system composed of a soluble iron compound plus a soluble ruthenium compound.

The Catalyst System

The ruthenium-containing compounds employed as a catalyst are selected from the group consisting of ruthenium salts of mineral acids and organic carboxylic acids. For instance, the ruthenium compound may be a salt of a mineral acid, such as ruthenium (III) chloride hydrate, ruthenium (III) bromide, ruthenium (III) iodide, tricarbonylruthenium nitrate, or as the salt of a suitable organic carboxylic acid, for example, ruthenium (III) acetate, ruthenium naphthenate, ruthenium valerate and ruthenium complexes with carbonyl-containing ligands such as ruthenium (III) acetylacetonate.

Additional examples of ruthenium compounds include ruthenium octoate, ruthenium laurate, ruthenium stearate, ruthenium linoleate, ruthenium nitrate, ruthenium sulfate and ruthenium carbonyl.

The iron-containing compounds employed as catalysts are selected from the group consisting of ferrous and ferric salts of mineral acids and organic carboxylic acids, such as ferrous and ferric compounds, including: iron (II) acetate, iron (III) acetate, iron (III) borate, iron (II) bromide, iron (II) chloride, iron (III) chloride, iron (III) 1,3-diphenyl-1,3-propanedionate, iron (III) 2-ethylhexanuate, iron (II) fluoride, iron (III) fluoride, iron (II) gluconate, iron (II) iodide, iron (III) nitrate, iron (III) 2,4-pentanedionate, iron (III) perchlorate, iron (II) sulfate, iron (III) sulfate.

The combined ruthenium plus iron compounds may comprise 0.001 to 10 wt. % of the total t-butyl hydroperoxide reactant mix. Preferably the ruthenium plus iron compounds comprise 0.01 to 5.0 wt. % of the total reactants.

Said ruthenium plus iron compounds may be charged to the hydroperoxide reactants in a weight ratio of iron to ruthenium of 0.01:1 to 100:1. Preferably this iron/ruthenium compound weight ratio is 1:1 to 10:1.

The process of the present invention may be conducted batchwise in kettles or by continuously passing the reactants through a tubular reactor.

The catalytic decomposition of the tertiary butyl hydroperoxide is preferably conducted at a temperature within the range of about 20° to about 100° C. and, more preferably, at a temperature within the range of about 30° to about 60° C. The reaction is preferably conducted at autogenous pressure although superatmospheric pressures up to about 1000 psig. may be used, if desired.

Flow rates of the charge solution to the reaction zone should be adjusted in order to provide an appropriate contact time within the reactor. In a batch process, the holding time may suitably be from about 0.5 to about 10 hours, and more preferably about 1 to 3 hours.

In accordance with the most preferred embodiment of the present invention, isobutane is reacted with oxygen in an oxidation zone under oxidation reaction conditions including a temperature of about 135° to about 155° C., a pressure of about 300 to about 800 psig., and a holding time of about 2 to about 6 hours to provide an initial oxidation reaction product comprising unreacted isobutane, tertiary butyl hydroperoxide, tertiary butyl alcohol, and oxygen-containing by-products. The oxidation reaction product is fractionated in any appropriate manner (e.g., by distillation in a distillation zone) to remove the isobutane therefrom for recycle and to provide a solution of tertiary butyl hydroperoxide and tertiary butyl alcohol which will normally contain from about 5 to about 30 wt. % of tertiary butyl hydroperoxide. If the tertiary butyl hydroperoxide concentration is excessive, additional tertiary butyl alcohol may be added.

The solvent solution of tertiary butyl alcohol in organic solvents (e.g., tertiary butyl alcohol solvent solution of tertiary butyl hydroperoxide) is then charged to a catalytic hydroperoxide decomposition zone where it is brought into contact with a catalyst system composed of a soluble ruthenium compound and a soluble iron compound to substantially selectively convert the tertiary butyl hydroperoxide to tertiary butyl alcohol with high yields and selectivities.

As indicated, the catalytic decomposition of the tertiary butyl hydroperoxide in the catalytic hydroperoxide decomposition reaction zone may suitably be conducted at a temperature within the range of about 20° to about 120° C. (and more preferably from about 30° to about 60° C.) at autogenous pressure or if desired at a superatmospheric pressure up to 1000 psig. for a contact time within the range of about 0.5 to about 10 hours, and more preferably about 1 to 3 hours.

The reaction product from the tertiary butyl hydroperoxide decomposition step may then be fractionated in any suitable manner, such as by extractive distillation to recover the tertiary butyl alcohol.

SPECIFIC EXAMPLES

The invention will be further illustrated by the following specific examples which are given by way of illustration and not as limitations on the scope of this invention.

Procedure: Tube Experiments

A 150-ml Fisher-Porter pressure tube equipped with pressure gauge, rupture disk, and shut-off valve was charged with 15.0 g of a 20% TBHP solution in TBA, and catalyst(s). The tube was suspended in a constant temperature bath (+ or −0.2° C.) for the desired period of time at the required temperature. The tube was then placed in cold water (15°–20° C.) for 15 minutes after which the pressure was slowly released. The liquid contents were analyzed by GC. The results are shown in the attached Table I.

TABLE I

| Notebook No. | Catalyst(s)[a] | | Time (Hr) | Temp (°C.) | Conv. TBHP% | Selectivity, % | | | |
|---|---|---|---|---|---|---|---|---|---|
| | | | | | | TBA | Acetone | MeOH | DTBP |
| 6224-63 | Ru(AcAc)$_3$ | [.005 g] | 1.0 | 100.0 | 99.87 | 78.56 | 19.75 | 5.65 | 0.91 |
| 6224-70 | Ru(AcAc)$_3$ | [.005 g] | 1.5 | 80.0 | 99.85 | 83.43 | 14.63 | 3.02 | 1.30 |
| 6224-75 | Ru(AcAc)$_3$ | [.005 g] | 4.0 | 60.0 | 99.92 | 86.49 | 10.91 | 1.57 | 1.99 |
| 6224-77 | Ru(AcAc)$_3$ | [.005 g] | 1.0 | 60.0 | 99.88 | 86.22 | 11.31 | 1.64 | 1.88 |
| 6224-80 | Ru(AcAc)$_3$ Fe(AcAc)$_3$ | [.005 g] [.01 g] | 1.0 | 60.0 | 99.64 | 87.53 | 9.78 | 1.33 | 2.07 |
| 6225-20 | Ru(AcAc)$_3$ Fe(AcAc)$_3$ | [.002 g] [.018 g] | 2.0 | 60.0 | 98.88 | 88.50 | 9.03 | 1.10 | 1.75 |
| 6225-21 | Ru(AcAc)$_3$ Fe(AcAc)$_3$ | [.004 g] [.036 g] | 2.0 | 60.0 | 98.48 | 88.51 | 9.29 | 1.32 | 1.57 |
| 6225-27[b] | Ru(AcAc)$_3$ Cr(AcAc)$_3$ | [.005 g] [.01 g] | 2.0 | 60.0 | 99.75 | 87.33 | 10.51 | 1.32 | 1.60 |
| 6225-48 | Ru(AcAc)$_3$ Fe(AcAc)$_3$ | [.004 g] [.036 g] | 2.0 | 40.0 | 89.84 | 91.13 | 4.78 | <0.5 | 3.30 |

[a]AcAc = Acetylacetonate
[b]U.S. Pat. No. 4,551,553 (ARCO)

With reference to the table, it will be noted that essentially equivalent conversions of the tertiary butyl hydroperoxide were obtained with the ruthenium catalyst, the reference ruthenium-chromium catalyst and the ruthenium-iron catalysts of the present invention and that essentially equivalent selectivities to tertiary butyl alcohol were also obtained. However, there was a significant and desirable reduction in the selectivity of the reaction to acetone with the ruthenium-iron catalysts of the present invention. Thus when the acetone selectivity for Run No. 6224-77 using a ruthenium catalyst is compared with the acetone selectivity for Run No. 6224-80 of the present invention, it will be noted that the acetone selectivity was reduced by about 15%. Acetone selectivities were also lower in Run No. 6225-20 and Run No. 6225-21, where reductions of about 20% and about 17%, respectively, were obtained. In Run No. 6225-48, conducted at a temperature of only about 40° C., there was a loss in the conversion of the tertiary butyl hydroperoxide which was offset by about a 5% increase in the selectivity to tertiary butyl alcohol and by about a 60% reduction in the selectivity to acetone.

Iron compounds are, in general, more economical and less toxic than similar chromium compounds. In addition, iron compounds do not have the handling and disposal problems that some chromium compounds have.

Having thus described our invention, what is claimed is:

1. In a method wherein a solution of a t-butyl hydroperoxide charge stock in t-butyl alcohol is brought into contact with a catalytically effective amount of a hydroperoxide decomposition catalyst in a hydroperoxide decomposition reaction zone in liquid phase with agitation to convert said t-butyl hydroperoxide to decomposition products, principally t-butyl alcohol, the improvement which comprises:
  (a) using, as said hydroperoxide decomposition catalyst, a soluble catalyst system consisting essentially of a soluble iron compound and a soluble ruthenium compound, and
  (b) recovering said t-butyl alcohol from the products of said hydroperoxide decomposition reaction,
  (c) said soluble iron compound being selected from the group consisting of ferrous and ferric salts of mineral acids and organic carboxylic acids,
  (d) said soluble ruthenium compound being selected from the group consisting of ruthenium salts of mineral acids and organic carboxylic acids.

2. A method as in claim 1 wherein the weight ratio of iron compound to ruthenium compound in the soluble catalyst system is within the range of about 1:1 to about 10:1.

3. A method as in claim 2 wherein the iron compound is ferrous acetylacetonate and the ruthenium compound is ruthenium acetylacetonate.

4. In a method for continuously preparing t-butyl alcohol wherein a charge stock is prepared comprising a solution of t-butyl hydroperoxide in t-butyl alcohol containing from about 5 to about 30 wt. % of t-butyl hydroperoxide, wherein said charge stock is continuously charged to a hydroperoxide decomposition zone, and wherein a catalyst hydroperoxide decomposition reaction is continuously conducted in said decomposition reaction zone to convert said t-butyl hydroperoxide to decomposition products, principally t-butyl alcohol, to provide a hydroxperoxide conversion product, the improvement which comprises:

(a) adding, as said decomposition catalyst, from about 0.01 to about 5 wt. %, based on the weight of the charge stock of a catalyst system consisting essentially of a soluble ruthenium catalyst compound and about 1 to about 10 parts by weight, based on the weight of the ruthenium compound of a soluble iron compound,
  (b) continuously conducting said hydroperoxide decomposition reaction in the presence of said hydroxperoxide decomposition catalyst system in said hydroperoxide decomposition zone in liquid phase with agitation under reaction conditions including a reaction time of about 0.5 to about 10 hours and a reaction temperature within the range of about 20° to about 100° C. and autogenous pressure,
  (c) continuously removing a stream of said hydroperoxide conversion product from said hydroperoxide conversion zone, and
  (d) continuously recovering t-butyl alcohol from said stream of said hydroxperoxide conversion product,
  (e) said soluble iron compound being selected from the group consisting of ferrous and ferric salts of mineral acids and organic carboxylic acids,
  (f) said soluble ruthenium compound being selected from the group consisting of ruthenium salts of mineral acids and organic carboxylic acids.

5. A method as in claim 4 wherein the iron compound is ferrous acetylacetonate and the ruthenium compound is ruthenium acetylacetonate.

6. A method as in claim 5 wherein the reaction time is within the range of about 1 to about 3 hours and the reaction temperature is within the range of about 30° to about 60° C.

* * * * *